US011164371B2

United States Patent
Yellin et al.

(10) Patent No.: US 11,164,371 B2
(45) Date of Patent: Nov. 2, 2021

(54) MARKING A COMPUTERIZED MODEL OF A CARDIAC SURFACE

(71) Applicant: Biosense Webster (Israel) Ltd., Yokneam (IL)

(72) Inventors: Tamir Avraham Yellin, Yokneam Hamoshava (IL); Roy Urman, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 117 days.

(21) Appl. No.: 15/848,535

(22) Filed: Dec. 20, 2017

(65) Prior Publication Data

US 2019/0188909 A1 Jun. 20, 2019

(51) Int. Cl.
*A61B 34/10* (2016.01)
*G06T 17/20* (2006.01)
(Continued)

(52) U.S. Cl.
CPC ............ *G06T 17/20* (2013.01); *A61B 5/0245* (2013.01); *A61B 5/0538* (2013.01); *A61B 5/062* (2013.01);
(Continued)

(58) Field of Classification Search
CPC ......... A61B 5/044; A61B 5/042; A61B 5/743; A61B 5/04012; A61B 5/0402; A61B 5/0006; A61B 5/742; A61B 5/00; A61B 5/0031; A61B 5/0408; A61B 5/05; A61B 5/6869; A61B 5/7285; A61B 5/7435; A61B 5/748; A61B 5/04; A61B 5/061;
(Continued)

(56) References Cited

U.S. PATENT DOCUMENTS 6,937,884 B1   8/2005 Barbour
7,245,962 B2 *  7/2007 Ciaccio .............. A61B 5/04011
                                               600/512
(Continued)

FOREIGN PATENT DOCUMENTS

WO   WO 08/035070 A2   3/2008

OTHER PUBLICATIONS

Bhakta, Deepak et al., "Review Article Principles of Electroanatomic Mapping", Jan. 1, 2008, www.http://images.biomedsearch.com/18270601/ipej080032-00.pdf?AWSAccessKeyId=AKIAIBOKHYOLP4MRGQ&Expires=1550361600&Signature=wCwV%2Bgilircp82PeM8nriUeB7og%3D , p. 43, figure 12.
(Continued)

Primary Examiner — Deborah L Malamud
(74) Attorney, Agent, or Firm — Dergosits & Noah LLP; Todd A. Noah

(57) ABSTRACT

Described embodiments include a system that includes an electrical interface and a processor. The processor is configured to receive, via the electrical interface, an electrocardiographic signal from an electrode within a heart of a subject, to ascertain a location of the electrode in a coordinate system of a computerized model of a surface of the heart, to select portions of the model responsively to the ascertained location, such that the selected portions are interspersed with other, unselected portions of the model, and to display the model such that the selected portions, but not the unselected portions, are marked to indicate a property of the signal. Other embodiments are also described.

20 Claims, 3 Drawing Sheets

(51) Int. Cl.
| | |
|---|---|
| *A61B 5/00* | (2006.01) |
| *A61B 5/0245* | (2006.01) |
| *A61B 5/0538* | (2021.01) |
| *A61B 5/06* | (2006.01) |
| *A61B 5/25* | (2021.01) |
| *A61B 5/287* | (2021.01) |
| *A61B 5/339* | (2021.01) |
| *A61B 5/349* | (2021.01) |
| *A61B 17/00* | (2006.01) |

(52) U.S. Cl.
CPC ............... *A61B 5/065* (2013.01); *A61B 5/25* (2021.01); *A61B 5/287* (2021.01); *A61B 5/339* (2021.01); *A61B 5/349* (2021.01); *A61B 5/6852* (2013.01); *A61B 5/7221* (2013.01); *A61B 5/7235* (2013.01); *A61B 5/7271* (2013.01); *A61B 5/743* (2013.01); *A61B 5/7425* (2013.01); *A61B 5/7435* (2013.01); *A61B 5/7485* (2013.01); *A61B 34/10* (2016.02); *A61B 5/7278* (2013.01); *A61B 2017/00053* (2013.01); *A61B 2034/105* (2016.02); *A61B 2562/04* (2013.01); *A61B 2562/06* (2013.01); *G06T 2210/41* (2013.01)

(58) Field of Classification Search
CPC . A61B 5/486; A61B 2576/023; A61B 5/0044; A61B 5/0077; A61B 5/066; A61N 1/08; A61N 1/36185; G06F 3/04815; G06F 3/04842; G06F 3/04847; G06F 19/34; G06T 2210/41; G08B 21/0453
See application file for complete search history.

(56) References Cited

U.S. PATENT DOCUMENTS

| | | |
|---|---|---|
| 8,478,393 B2 | 7/2013 | Ramanathan et al. |
| 8,647,284 B2 | 2/2014 | Afonso |
| 2014/0323848 A1 | 10/2014 | He et al. |

OTHER PUBLICATIONS

Alessandrini, Martino et al., A Computational Framework to Benchmark Basket Catheter Guided Ablation, 2016 Computing in Cardiology Conference (CINC), vol. 44, Sep. 14, 2017.

European Search Report dated Feb. 22, 2019 from corresponding European Patent Application No. 18213827.1.

Wilson, Kevin et al., "Mapping of Cardiac Electrophysiology onto a Dynamic Patient Specific Heart Model", IEEE Transactions on Medical Imaging, vol. 28, No. 12, Dec. 1, 2009, pp. 1870-1880.

Gupta, Anoop Kumar et al., "Cardiac Mapping: Utility or Futility?", Indian Pacing and Electrophysiology Journal, Jan. 1, 2002, pp. 20-32, Netherlands.

Bhakta, Deepak et al., "Review Article Principles of Electroanatomic Mapping", Jan. 1, 2008, www. http://imaaes.biomedsearch.eom/18270601/ipej080032-00.pdf?AWSAccessKeyId=:::AKIAiBOKHYOLP4MBiViRGQ&Expires:=1550361SOO&Signature==wCwV%2Bgilircp82PeM8nriUeB7og%3D , p. 43, figure 12.

* cited by examiner

MARKING A COMPUTERIZED MODEL OF A CARDIAC SURFACE

FIELD OF THE INVENTION

The present invention relates to the display of electroanatomical information.

BACKGROUND

In some electroanatomical mapping procedures, a catheter, comprising one or more electrodes, is inserted into the heart, and the electrodes are then used to acquire intracardiac electrocardiographic (ECG) signals from the surface of the heart.

SUMMARY OF THE INVENTION

There is provided, in accordance with some embodiments of the present invention, a system that includes an electrical interface and a processor. The processor is configured to receive, via the electrical interface, an electrocardiographic signal from an electrode within a heart of a subject, to ascertain a location of the electrode in a coordinate system of a computerized model of a surface of the heart, to select portions of the model responsively to the ascertained location, such that the selected portions are interspersed with other, unselected portions of the model, and to display the model such that the selected portions, but not the unselected portions, are marked to indicate a property of the signal.

In some embodiments, the processor is configured to select the portions of the model by:

projecting a plurality of rays from the ascertained location, and selecting the portions of the model in response to points at which the rays intersect the model.

In some embodiments, the processor is configured to, in selecting the portions of the model, set a density of the selected portions as a decreasing function of a distance from the model of the ascertained location.

In some embodiments, the processor is configured to, in selecting the portions of the model, set a spread of the selected portions as an increasing function of a distance, from the model, of the ascertained location.

In some embodiments, the signal is a first signal and the electrode is a first electrode, the processor is further configured to receive a second electrocardiographic signal from a second electrode within the heart, and the processor is configured to display the model such that at least some of the other portions of the model are marked to indicate the property of the second signal.

In some embodiments, the property is a first property, and the processor is configured to display the model such that at least some of the other portions of the model are marked to indicate a second property of the signal.

In some embodiments, the processor is configured to display the model such that the selected portions of the model are colored to indicate the property.

In some embodiments, the property of the signal is a dominant frequency of the signal.

In some embodiments, the processor is configured to, in selecting the portions of the model, set a density of the selected portions responsively to a feature of a frequency spectrum of the signal at the dominant frequency.

In some embodiments, the processor is configured to, in selecting the portions of the model, set a spread of the selected portions responsively to a feature of a frequency spectrum of the signal at the dominant frequency.

In some embodiments, the property of the signal is a cycle length of the signal.

In some embodiments, the processor is configured to select the portion of the model such that a density of the selected portions decreases with distance from a point on the model that is closest to the ascertained location.

There is further provided, in accordance with some embodiments of the present invention, a method that includes receiving, by a processor, an electrocardiographic signal from an electrode within a heart of a subject, ascertaining a location of the electrode in a coordinate system of a computerized model of a surface of the heart, selecting portions of the model responsively to the ascertained location, such that the selected portions are interspersed with other, unselected portions of the model, and displaying the model such that the selected portions, but not the unselected portions, are marked to indicate a property of the signal.

The present invention will be more fully understood from the following detailed description of embodiments thereof, taken together with the drawings, in which:

DETAILED DESCRIPTION OF EMBODIMENTS

Overview

Figure 1:
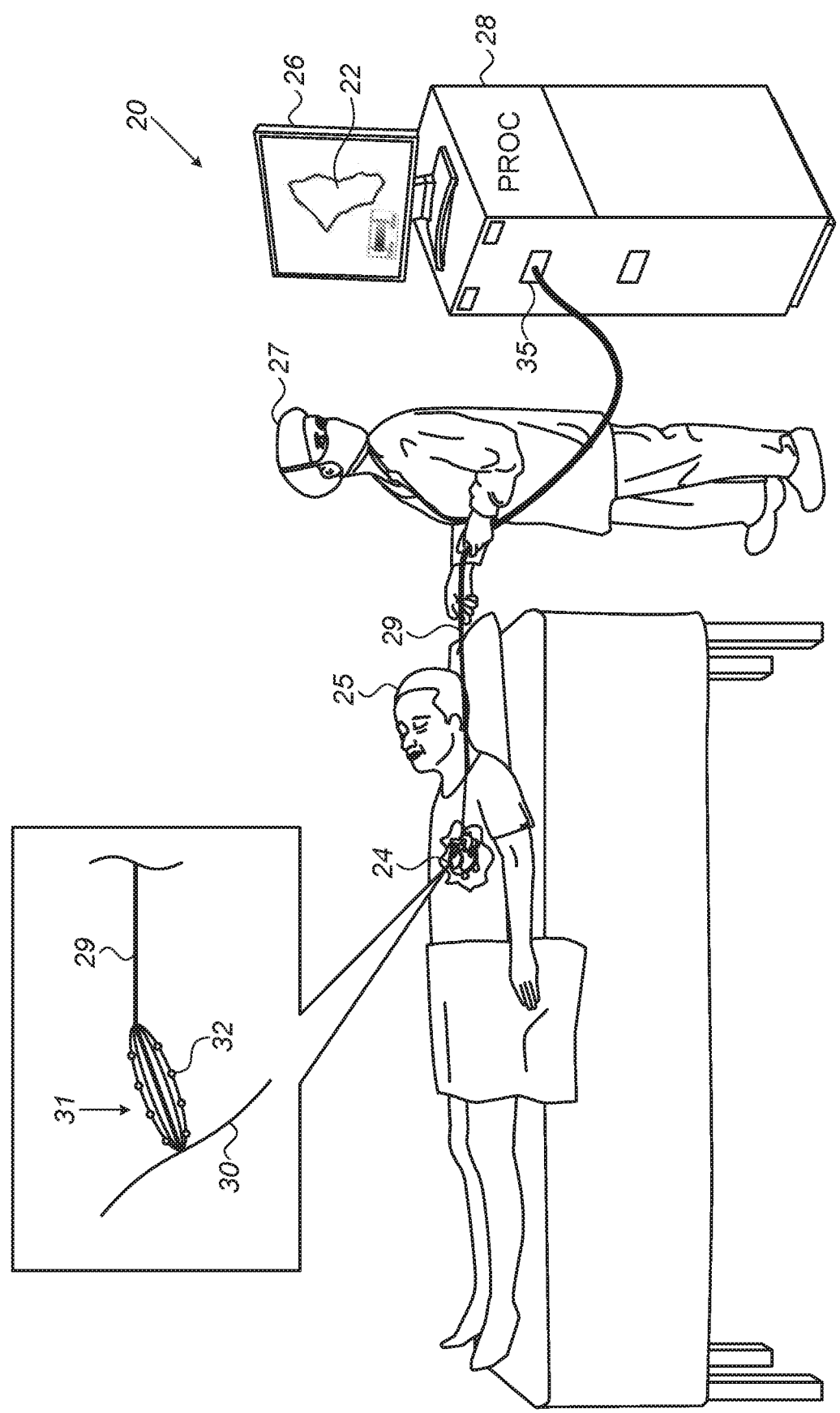
FIG. 1 is a schematic illustration of a system for displaying a computerized model of a surface of a heart of a subject, in accordance with some embodiments of the present invention.

Embodiments described herein include techniques for displaying electroanatomical information, whereby a computerized anatomical model of a surface of a heart is "sprayed" with colors, and/or other markings, indicating electrical properties of the surface. Per these techniques, for each electrode that acquires an ECG signal from the surface, a processor ascertains the location of the electrode in the coordinate system of a model of the surface. The processor then marks some portions of the model in the vicinity of this location, to indicate a property, such as a dominant frequency, of the ECG signal. The density and/or spread of the marked portions may be a function of the distance of the electrode's location from the model, of various features of the signal, and/or of the portions' locations. For example:

(i) The density of the marked portions may be a decreasing function of the distance of the electrode's location from the model. Alternatively or additionally, the spread of the marked portions—i.e., the amount of surface area on the model that is covered at least partly by the marked portions—may be an increasing function of this distance. By changing the density and/or spread of the marked portions as a function of the distance of the electrode from the model, the processor provides the physician with an intuitive visual indication of this distance, which in turn reflects the quality of the acquired ECG signal. (The quality increases as the distance decreases.)

(ii) When marking the model to show a dominant frequency, the density and/or spread of the marked portions may be an increasing function of the amplitude and/or width of the frequency spectrum of the signal at the dominant frequency. The physician is thus provided with an intuitive indication of the amplitude and/or width at the dominant frequency.

(iii) The density of the marked portions may decrease with distance from the point on the model that is closest to the electrode's location.

The techniques described herein are particularly helpful for displaying regions of tissue that lie between two electrodes. For example, if two electrodes record, respectively, two different dominant frequencies, the model may be colored in a first color at the point that is closest to the first electrode, in a second color at the point that is closest to the second electrode, and in both colors—interspersed with one another—between the two electrodes. (The relative dominance of one color over the other in this intermediate region may be a function of any of the factors described above, such as distance from each of the closest points, and/or the respective amplitudes of the two frequency spectra at their respective dominant frequencies.) This provides a more accurate representation of the cardiac surface, relative to other, hypothetical techniques that are not within the scope of the present disclosure.

For example, one hypothetical technique might interpolate the two colors, such that the region between the electrodes is shown in varying degrees of interpolation. For example, if one electrode records 12 Hz and another electrode records 18 Hz, 12 Hz may be mapped to red, 18 Hz may be mapped to blue, and the region between the two electrodes may be shown in varying shades of purple. Such interpolation, however, may be misleading, as it implies that the cardiac surface exhibits dominant ECG frequencies between 12 Hz and 18 Hz. In contrast, embodiments of the present invention may color the intermediate region in both red and blue, but not in purple, indicating that this region exhibits dominant ECG frequencies of both 12 Hz and 18 Hz, but not frequencies between 12 Hz and 18 Hz.

Although the present description relates mainly to electroanatomical mapping applications, it is noted that the techniques described herein may be used for any suitable application that requires extrapolating, over a surface, measurements that were acquired at discrete points on the surface.

System Description

Reference is initially made to FIG. 1, which is a schematic illustration of a system 20 for displaying a computerized model 22 of a surface 30 of a heart 24 of a subject 25, in accordance with some embodiments of the present invention.

FIG. 1 depicts the performance of an electroanatomical mapping procedure, whereby a physician 27 navigates a catheter 29 within heart 24, and, for various positions of the catheter, a plurality of electrodes 32 at the distal end of catheter 29 record intracardiac ECG signals from surface 30 of the heart. Typically, catheter 29 is equipped with one or more position sensors (not shown), such that each recorded ECG signal may be associated with the location of the electrode 32 that performed the recording. For example, catheter 29 may comprise one or more electromagnetic position sensors, which, in the presence of an external magnetic field, generate signals that vary with the respective positions of the sensors. Alternatively, to track the position of each electrode 32, the processor may ascertain the respective impedances between the electrode and a plurality of electrodes coupled externally to subject 25 at various different locations, and then compute the ratios between these impedances. As yet another alternative, the processor may use both electromagnetic tracking and impedance-based tracking, as described, for example, in U.S. Pat. No. 8,456, 182, whose disclosure is incorporated herein by reference.

In some embodiments, as shown in FIG. 1, catheter 29 is a basket catheter comprising, at its distal end, a basket 31 of electrodes 32. Alternatively, catheter 29 may have any other suitable form, with electrodes 32 being arranged in any suitable configuration.

System 20 comprises a processor (PROC) 28 and a display 26. As the ECG signals are acquired, the signals are passed, via catheter 29 and an electrical interface 35 (such as a port or socket), to processor 28. Processor 28 uses the signals, along with the associated electrode-location information, to mark model 22 to indicate electrical properties of surface 30, as described in detail below. During and/or following the mapping procedure, processor 28 may display model 22 on display 26.

In general, processor 28 may be embodied as a single processor, or as a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
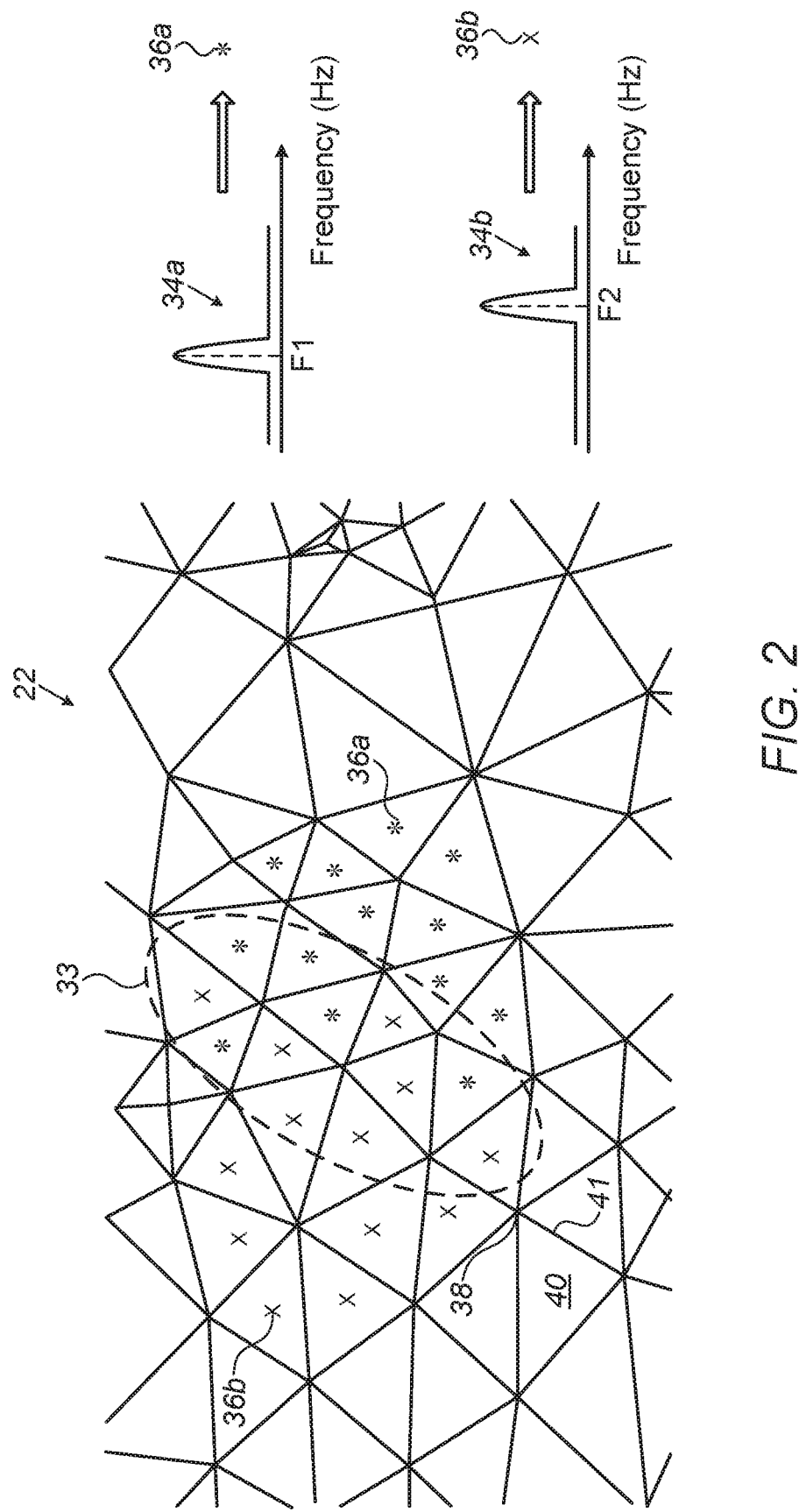
FIG. 2 is a schematic illustration of a portion of a computerized model of a surface of a heart, in accordance with some embodiments of the present invention.

Reference is now made to FIG. 2, which is a schematic illustration of a portion of model 22 of surface 30, as displayed by processor 28, in accordance with some embodiments of the present invention. Typically, model 22 models the anatomical features of surface 30 by a tessellation of tiles 40, having any suitable shape (such as a triangular shape), which abut each other along edges 41 and vertices 38. (In practice, edges 41 and vertices 38 are not displayed on-screen.)

As described above with reference to FIG. 1, processor 28 receives ECG signals from electrodes 32 during the electroanatomical mapping procedure. Further to receiving these signals, processor 28 computes the respective spectra of these signals, and/or process the signals in any other suitable manner, to ascertain a property of the signals (and hence, of the tissue from which the signals were acquired). For example, the processor may ascertain the respective dominant frequencies of the signals, and/or the respective cycle lengths of the signals. The processor then designates a different respective color, or other marking, to represent the property of each of the signals. Subsequently, as described in detail below with reference to FIGS. 3-4, for each of the signals, the processor selects portions of the model responsively to the location of the electrode that acquired the signal, and then displays model 22 such that the selected portions (but not any unselected portions) of the model are marked, using the designated marking, to indicate the property.

For example, FIG. 2 shows a first frequency spectrum 34a, derived from a first ECG signal received from a first electrode, and a second frequency spectrum 34b, derived from a second ECG signal received from a second electrode. From spectrum 34a, processor 28 ascertains that the first signal has a dominant frequency of F1, and from spectrum 34b, the processor ascertains that the second signal has a dominant frequency of F2. (In the context of the present application, including the claims, a "dominant frequency" may be any frequency at which the relevant frequency spectrum attains a local maximum value.) Accordingly, the processor selects a first indicator 36a to represent frequency F1, and a second indicator 36b to represent frequency F2. Subsequently, the processor marks selected portions of model 22, by overlaying first indicator 36a or second indicator 36b on the each of the selected portions.

Each of the indicators used for marking the model may include any suitable symbol(s), such as the symbols shown in FIG. 2, and/or any suitable character(s). For example, alternatively to using the symbols shown in FIG. 2, the processor may overlay each selected portion of the model with the value of F1 or F2, e.g., by overlaying "12" to indicate a dominant frequency of 12 Hz. As another alternative, the processor may designate a first color to represent frequency F1 and a second color to represent frequency F2, and then display the model such that each of the selected portions of the model is colored, in either the first color or the second color, to indicate frequency F1 or frequency F2. (The processor may further display a key, which indicates the meaning of each of the colors or indicators.)

In some embodiments, as shown in FIG. 2, each of the selected portions of model 22 comprises a respective tile 40. That is, the processor colors, and/or overlays an appropriate indicator on, each selected tile 40. Alternatively or additionally, the processor may mark selected vertices 38, by coloring, and/or overlaying an appropriate indicator on, each selected vertex.

As noted above in the Overview, in general, using the techniques described herein, the model is "sprayed" with color and/or with other markings, such that portions of the model marked with a first type of marking may be interspersed with other portions of the model that are marked with a second type of marking, or are not marked at all. For example, FIG. 2 shows a region 33 of the model in which two kinds of markers are interspersed with one other. As noted above in the Overview, interspersing the markers in this manner provides a more accurate visual representation of the electrical properties of the tissue, relative to other techniques that use interpolation.

It is noted that the scope of the present disclosure includes processing the signals from the electrodes, and marking model 22 in response thereto, in real-time, i.e., during the procedure as the data are collected, and/or offline, subsequently to the procedure.

Figure 3:
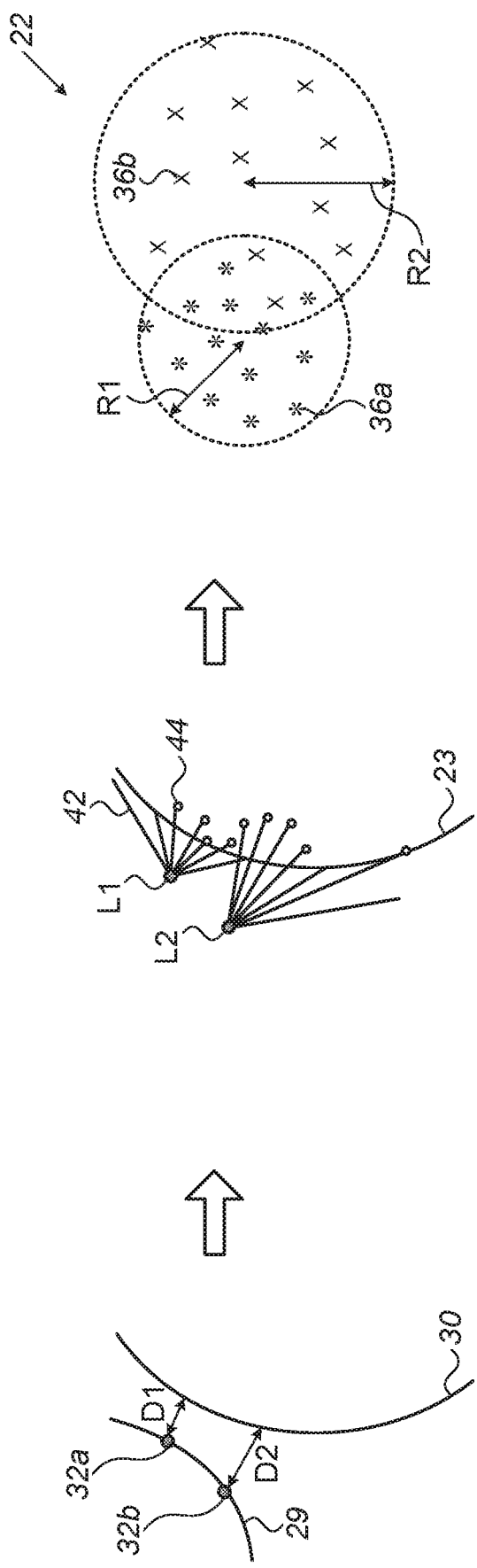
FIGS. 3-4 are schematic illustrations of techniques for displaying a computerized model of a surface of a heart, in accordance with some embodiments of the present invention.

Reference is now made to FIG. 3, which is a schematic illustration of a technique for displaying model 22, in accordance with some embodiments of the present invention.

The left portion of FIG. 3 shows an arm of catheter 29, comprising a first electrode 32a and a second electrode 32b, positioned near surface 30 of the heart. First electrode 32a is at a first distance D1 from the surface, while second electrode 32b is at a second distance D2 from the surface, D2 being greater than D1. At these positions, electrodes 32a and 32b acquire ECG signals from surface 30.

As described above with reference to FIG. 1, processor 28 ascertains the location of each of the electrodes in the coordinate system of model 22. Accordingly, the middle portion of FIG. 3 shows the location L1 of first electrode 32a and the location L2 of second electrode 32b in the coordinate system of model 22, as ascertained by the processor.

After ascertaining the electrodes' locations, the processor projects a plurality of rays 42 from each of the ascertained locations, as further shown in the middle portion of FIG. 3. For example, considering the location of the electrode as the center of a sphere, the processor may project a different respective ray 42 for each pair of angles ($\theta$, $\varphi$), where $\theta$ (the polar angle in spherical coordinates) runs between 0 and 180 degrees with a given step size (e.g., 5 or 10 degrees), and $\varphi$ (the azimuthal angle in spherical coordinates) runs between 0 and 360 degrees with another given step size (e.g., 5 or 10 degrees), such that rays 42 are projected in a spherical formation.

For each set of projected rays, the processor selects portions of the model in response to the points 44 at which the rays intersect the model. For example, the processor may select each tile that is struck by at least one of the rays. (If a given tile is struck by two rays projected from different respective electrode locations, the processor may randomly choose one of the rays as the "winner" of the collision.) Alternatively, for each of intersection points 44, the processor may select the vertex that is closest to the intersection point.

Subsequently to selecting the relevant portions of model 22, the processor displays model 22 such that, for each of the electrodes, portions of the model selected for the electrode are marked to indicate a property, such as a dominant frequency, of the signal that was received from the electrode. For example, as shown at the right portion of FIG. 3, the processor may render model 22 such that each of the selected portions for electrode 32a are marked with indicator 36a to indicate a property of the ECG signal from electrode 32a, and each of the selected portions for electrode 32b are marked with indicator 36b to indicate the property of the signal from electrode 32b. (For simplicity, the anatomical details of model 22 are not shown in FIG. 3 or FIG. 4.)

A result of using the above-described ray-projection technique is that, for each of the electrodes, the density of the selected (and marked) portions is a decreasing function of the distance from the model of the ascertained location of the electrode. (This "density" may be quantified, for example, as the number of selected portions per unit of surface area of model 22, or per unit of area on display 26.) A further result of the ray-projection technique is that the spread of the selected (and marked) portions is an increasing function of the distance from the model of the ascertained location of the electrode. (This "spread" may be quantified, for example, as the geodesic distance along the surface of the model, or the distance along display 26, from the point on the model that is closest to the electrode's location, to the selected portion that is farthest from this closest point.)

For example, in FIG. 3, indicators 36a are at a greater density than are indicators 36b, as a result of the smaller distance of electrode 32a from surface 30, relative to electrode 32b. Likewise, while indicators 36a are enclosed by a circle having a smaller radius R1, indicators 36b are enclosed only by a circle having a larger radius R2.

Notwithstanding the particular example technique described above, it is noted that the scope of the present disclosure includes any suitable technique for setting the density as a decreasing function of the distance of the electrode's location from the model, and/or setting the spread as an increasing function of this distance.

Figure 4:
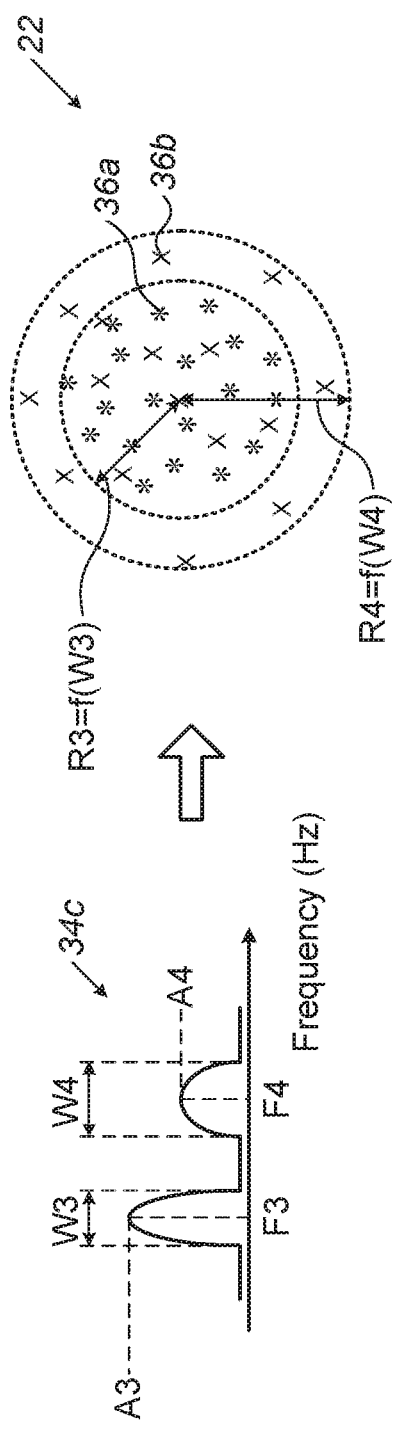

Reference is now made to FIG. 4, which is a schematic illustration of another technique for displaying model 22, in accordance with other embodiments of the present invention.

FIG. 4 illustrates a scenario in which a single electrode captures an ECG signal whose spectrum 34c exhibits two dominant frequencies: a first dominant frequency F3, and a second dominant frequency F4. In response to identifying these two dominant frequencies, the processor selects two indicators (or colors), one indicator (or color) for each of the frequencies. In the particular case shown, the processor selects indicator 36a for F3, and indicator 36b for F4. The processor then displays model 22 such that portions of the model marked to indicate frequency F3 are interspersed with other portions of the model marked to indicate frequency F4. This provides the physician with an intuitive visual indication of the two different dominant frequencies.

In general, the above-described technique may be applied to any scenario in which two different properties of an ECG signal—such as two different cycle lengths—are ascertained. In other words, some portions of the model in the vicinity of the electrode may be marked to indicate the first property, while other portions of the model, which are interspersed with the former portions, may be marked to indicate the second property. This technique may be similarly applied in cases in which more than two properties of the signal are ascertained.

FIG. 4 further illustrates that the density and spread of the selected (and marked) portions of the model may be set responsively to features of frequency spectrum 34c at the respective dominant frequencies of the signal. For example, for each of the dominant frequencies, the density of the selected portions may be an increasing function of the amplitude of the frequency spectrum at the dominant frequency. FIG. 4 illustrates such an embodiment, by showing the marking density for frequency F3, which has a larger amplitude A3, as being greater than the marking density for frequency F4, which has a smaller amplitude A4. Alternatively or additionally, the spread may be an increasing function "f" of the width of the frequency spectrum at the dominant frequency. FIG. 4 illustrates such an embodiment, by showing the spread for frequency F4, quantified by a radius R4, being greater than the spread for frequency F3, quantified by the radius R3, as a result of the greater width W4 of the spectrum at F4, relative to the width W3 at F3. (The width may be quantified, for example, as a full width at half maximum.)

Notwithstanding the specific embodiments described above, it is noted that, when marking to indicate a dominant frequency, each of the density and spread of the marking may be any suitable increasing or decreasing function of the amplitude at the dominant frequency, the width at the dominant frequency, and/or any other suitable feature of the signal in the time- or frequency-domain. Likewise, when marking to indicate any other property of the signal (such as a cycle length), each of the density and spread may be set by applying any suitable function to any suitable feature(s) of the signal in the time- or frequency-domain.

In some embodiments, to perform the techniques described above with reference to FIG. 4, the processor first finds the point on the model that is closest to the location of the electrode. The processor then calculates the maximum geodesic distance from the closest point at which a portion of the model may potentially be marked. (This distance corresponds to the marking spread.) The processor then iterates over all relevant portions (e.g., over all tiles or vertices) of the model within the calculated distance of the closest point, and decides, based on the desired marking density, whether to mark the portion. For example, the processor may generate a random number, and then compare the random number to a threshold that is a function of the desired marking density. In response to this comparison, the processor may decide whether to mark the portion. (Alternatively or additionally to the threshold being a function of the desired marking density, the distribution from which the random number is generated may be a function of the desired marking density.)

For example, for each relevant portion of the model within the calculated distance of the closest point, the processor may generate a random number from a uniform distribution between 0 and 1. The processor may then ascertain whether this number is less than a particular threshold. If yes, the processor may mark the portion; otherwise, the processor may refrain from marking the portion. The threshold may be closer to 1 for a higher marking density, and closer to 0 for a lower marking density. Alternatively, more complex algorithms may be used for determining the distribution of the marked portions of the model.

Alternatively or additionally to setting the density responsively to features of the signal, the density may decrease with distance from the point on the model that is closest to the location of the electrode.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for enhancing anatomical mapping by indicating electrical properties of the surface of the anatomy, comprising:
   an electrical interface; and
   a processor, configured to:
      receive, via the electrical interface, a first electrocardiographic signal from a first electrode and a second electrocardiographic signal from a second electrode within a heart of a subject,
      ascertain a property of each of the first and second signal,
      ascertain locations of the first and second electrodes in a coordinate system of a computerized model of the anatomical features of a surface of the heart,
      select portions of the model responsively to the ascertained locations, such that the selected portions are interspersed with other, unselected portions of the model by projecting a plurality of rays from each of the ascertained locations and selecting the portions of the model in response to the points at which the rays intersect the model; and display the model such that for each of the first and second electrodes, the portions of the model selected for each electrode are marked to indicate a corresponding property of the signal that was received from the corresponding electrode.

2. The system according to claim 1, wherein the property is a first property, and wherein the processor is configured to display the model such that at least some of the other portions of the model are marked to indicate a second property of the signal.

3. The system according to claim 1, wherein the processor is configured to display the model such that the selected portions of the model are colored to indicate the property.

4. The system according to claim 1, wherein the property of the signal is a dominant frequency of the signal.

5. The system according to claim 4, wherein the processor is configured to, in selecting the portions of the model, set a density of the selected portions responsively to a feature of a frequency spectrum of the signal at the dominant frequency.

6. The system according to claim 4, wherein the processor is configured to, in selecting the portions of the model, set a spread of the selected portions responsively to a feature of a frequency spectrum of the signal at the dominant frequency.

7. The system according to claim 1, wherein the property of the signal is a cycle length of the signal.

8. The system according to claim 1, wherein the processor is configured to select the portion of the model such that a density of the selected portions decreases with distance from a point on the model that is closest to the ascertained location.

9. The system according to claim 1, wherein the processor is configured to, in selecting the portions of the model, set a density of the selected portions as a decreasing function of a distance from the model of the ascertained location.

10. The system according to claim 1, wherein the processor is configured to, in selecting the portions of the model, set a spread of the selected portions as an increasing function of a distance, from the model, of the ascertained location.

11. A method for enhancing anatomical mapping by indicating electrical properties of the surface of the anatomy, comprising:
receiving, by a processor, a first electrocardiographic signal from a first electrode and a second electrocardiographic signal from a second electrode within a heart of a subject;
ascertaining a property of each of the first and second signal;
ascertaining locations of the first and second electrodes in a coordinate system of a computerized model of the anatomical features of a surface of the heart;
selecting portions of the model responsively to the ascertained locations, such that the selected portions are interspersed with other, unselected portions of the model by projecting a plurality of rays from each of the ascertained locations and selecting the portions of the model in response to the points at which the rays intersect the model; and
displaying the model such that for each of the first and second electrodes, the portions of the model selected for each electrode are marked to indicate a corresponding property of the signal that was received from the corresponding electrode.

12. The method according to claim 11, wherein the property is a first property, and wherein displaying the model comprises displaying the model such that at least some of the other portions of the model are marked to indicate a second property of the signal.

13. The method according to claim 11, wherein displaying the model comprises displaying the model such that the selected portions of the model are colored to indicate the property.

14. The method according to claim 11, wherein the property of the signal is a dominant frequency of the signal.

15. The method according to claim 14, wherein selecting the portions of the model comprises setting a density of the selected portions responsively to a feature of a frequency spectrum of the signal at the dominant frequency.

16. The method according to claim 14, wherein selecting the portions of the model comprises setting a spread of the selected portions responsively to a feature of a frequency spectrum of the signal at the dominant frequency.

17. The method according to claim 11, wherein the property of the signal is a cycle length of the signal.

18. The method according to claim 11, wherein selecting the portions of the model comprises selecting the portions of the model such that a density of the selected portions decreases with distance from a point on the model that is closest to the ascertained location.

19. The method according to claim 11, wherein selecting the portions of the model comprises setting a density of the selected portions as a decreasing function of a distance from the model of the ascertained location.

20. The method according to claim 11, wherein selecting the portions of the model comprises setting a spread of the selected portions as an increasing function of a distance, from the model, of the ascertained location.

* * * * *